(12) United States Patent
Delaloye et al.

(10) Patent No.: US 10,695,175 B2
(45) Date of Patent: Jun. 30, 2020

(54) METHOD AND APPARATUS USEFUL FOR TRANSCATHETER AORTIC VALVE IMPLANTATION

(71) Applicant: Symetis SA, Ecublens VD (CH)

(72) Inventors: Stephane Delaloye, Bulach (CH);
Jean-Luc Hefti, Cheseaux-Noreaz (CH); Youssef Biadillah, Lausanne (CH)

(73) Assignee: Boston Scientific Limited, Hamilton (BM)

( * ) Notice: Subject to any disclaimer, the term of this patent is extended or adjusted under 35 U.S.C. 154(b) by 384 days.

(21) Appl. No.: 15/072,628

(22) Filed: Mar. 17, 2016

(65) Prior Publication Data
US 2016/0193047 A1     Jul. 7, 2016

Related U.S. Application Data

(62) Division of application No. 13/978,679, filed as application No. PCT/EP2012/050303 on Jan. 10, 2012, now abandoned.

(30) Foreign Application Priority Data

Jan. 11, 2011    (EP) .................................... 11000150
Jan. 12, 2011    (EP) .................................... 11150746

(51) Int. Cl.
*A61F 2/24*         (2006.01)
*A61M 25/06*      (2006.01)
(Continued)

(52) U.S. Cl.
CPC ............ *A61F 2/2436* (2013.01); *A61F 2/243* (2013.01); *A61F 2/2427* (2013.01);
(Continued)

(58) Field of Classification Search
CPC .. A61M 2025/0024; A61M 2025/0025; A61M 25/0662; A61M 25/005;
(Continued)

(56) References Cited

U.S. PATENT DOCUMENTS

| 4,723,549 A | 2/1988 | Wholey et al. |
| 5,911,702 A * | 6/1999 | Romley ............. A61B 17/3439 604/171 |

(Continued)

FOREIGN PATENT DOCUMENTS

| EP | 0818214 A2 | 1/1998 |
| WO | 2005049125 A1 | 6/2005 |

OTHER PUBLICATIONS

European Search Report dated Feb. 21, 2020 for European Application No. 19193834.9-1132.

*Primary Examiner* — Katherine H Schwiker
(74) *Attorney, Agent, or Firm* — Seager, Tufte & Wickhem LLP (57) ABSTRACT

A guide catheter is described for introduction into a patient's vasculature, to provide a substantially continuous guide lumen within the vasculature to the ascending aorta, through which one or more other functional catheters may be introduced and removed during the procedure. The guide catheter includes an aligner at its distal region for aligning the position and/or inclination of the distal region of the guide catheter with respect to the ascending aorta. The aligner includes an embolic protection filter. The guide catheter is made of material collapsible/distensible in cross section to adopt a small shape when no catheter is present inside, and to distend to a large shape to accommodate passage of functional catheter therethrough. The cross-section shape collapses/distends by folding/unfolding of material without elastic stretching of the material.

5 Claims, 9 Drawing Sheets

(51) Int. Cl.
*A61M 25/10* (2013.01)
*A61M 25/00* (2006.01)

(52) U.S. Cl.
CPC . *A61M 25/0662* (2013.01); *A61F 2210/0057* (2013.01); *A61F 2310/00011* (2013.01); *A61F 2310/00017* (2013.01); *A61F 2310/00023* (2013.01); *A61M 25/005* (2013.01); *A61M 2025/0024* (2013.01); *A61M 2025/1047* (2013.01)

(58) Field of Classification Search
CPC .......... A61M 25/0012; A61M 25/0023; A61M 25/0026; A61M 25/0028; A61M 25/0029; A61M 25/003; A61M 25/0032; A61M 25/0051; A61M 25/0052; A61M 25/0053; A61M 25/0072; A61M 2025/0031; A61M 2025/0034; A61M 2025/0035; A61M 2025/0036; A61M 2025/0037; A61M 2025/0039; A61M 2025/004; A61M 2025/0681; A61M 2025/0687; A61M 2025/0063; A61F 2/2427; A61F 2/243; A61F 2/2433; A61F 2/2436; A61F 2/2439; A61F 2/95; A61F 2002/011; A61F 2002/016; A61F 2002/9528; A61B 17/3439; A61B 17/3431; A61B 17/12122; A61B 17/12172; A61B 17/3421; A61B 2017/3433; A61B 2017/3435; A61B 2017/3443; A61B 2017/3445; A61B 2017/3425; A61B 2017/00623
See application file for complete search history.

(56) References Cited

U.S. PATENT DOCUMENTS

| | | | |
|---|---|---|---|
| 6,358,238 B1* | 3/2002 | Sherry | A61M 25/0023 604/524 |
| 7,422,579 B2 | 9/2008 | Wahr et al. | |
| 2005/0125021 A1* | 6/2005 | Nance | A61B 17/3417 606/192 |
| 2005/0148929 A1 | 7/2005 | Gingles | |
| 2006/0135981 A1 | 6/2006 | Lenker et al. | |
| 2006/0270978 A1* | 11/2006 | Binmoeller | A61B 17/3431 604/104 |
| 2007/0050012 A1 | 3/2007 | Densford | |
| 2007/0118079 A1 | 5/2007 | Moberg et al. | |
| 2007/0249997 A1 | 10/2007 | Goodson et al. | |
| 2008/0243081 A1 | 10/2008 | Nance et al. | |
| 2009/0240202 A1* | 9/2009 | Drasler | A61M 25/0023 604/164.03 |
| 2009/0287182 A1 | 11/2009 | Bishop et al. | |
| 2011/0282353 A1* | 11/2011 | McHugo | A61B 1/00135 606/108 |

* cited by examiner

METHOD AND APPARATUS USEFUL FOR TRANSCATHETER AORTIC VALVE IMPLANTATION

RELATED APPLICATIONS

This application is a divisional of U.S. application Ser. No. 13/978,679, which is a national phase of PCT/EP2012/050303, filed 30 Sep. 2013, through which priority is also claimed to EP Application No. 11 000 150.0, filed 11 Jan. 2011, and to EP Application NO. 11 150 746.3, filed 12 Jan. 2011. The entire contents of each of these application are incorporated herein by reference.

FIELD OF THE INVENTION

The present invention relates to methods and apparatus useful for transcatheter aortic valve implantation (TAVI). In some non-limiting aspects, the invention is directed to implantation via a transvascular access to the heart.

BACKGROUND TO THE INVENTION

Traditional approaches for aortic valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to reduce invasiveness by using a transcatheter procedure, namely by delivering and implanting a prosthetic valve via a catheter inserted through a smaller skin incision, using either a transvascular route or a transapical route to the valve implantation site. The prosthetic valve (also referred to herein as a stent-valve) comprises a valve component and a stent component for anchoring the valve component at the desired implantation site.

While less invasive and arguably less complicated, transcatheter heart valve replacement procedures still face various difficulties. One issue encountered with a transvascular route is difficulty of navigating, along a tortuous and often stenosed vasculature, a delivery catheter large enough to accommodate a prosthetic valve for implantation. The distal end of the delivery catheter is typically in the range of 6-8 mm in diameter (18-24 French) to accommodate the prosthetic valve. The design of a delivery catheter has to address requirements for (i) atraumatic introduction, navigation and later withdrawal through the vasculature, and (ii) support, for example, for applying force along the length of the catheter from the proximal end, to traverse the existing valve, and manipulate the distal end to unsheath and deploy the prosthetic valve. These requirements often conflict, leading to compromises in design. For example, softness and flexibility of the catheter are desired for autraumaticity and ease of navigation, but reduce the ability of the catheter to provide support for force applied from the proximal end remotely to the distal end.

A further issue is the difficulty of remotely positioning the delivery catheter at an optimum position for deploying the prosthetic valve. If the prosthetic valve is not placed in the proper position relative to the implantation site, it can lead to poor functioning of the valve, or require further surgery to remedy. Incorrect positioning can, for example, lead to one or more complications including: valve regurgitation, instability, valve prolapse, reduced valve aperture, coronary occlusion, mitral valve interaction, and/or heart disfunction requiring the patient to be fitted with a pacemaker.

A further difficulty exacerbating the above is that patients selected for a transcatheter procedure are often those patients not considered suitable candidates for the more traditional, major surgical procedure. For example, such patients may be elderly, frail, suffer one or more morbidities that preclude major surgery and/or that present an unacceptable risk of mortality post surgery. The vasculatures of such patients may be highly calcified, tortuous, stenosed and/or fragile, complicating the process of introducing and advancing the delivery catheter to the implantation site, and increasing the risk of dislodging calcification into the blood stream, and the associated risks of embolisms and even stroke.

The present invention has been devised bearing such issues in mind.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

Broadly speaking, one aspect of the present invention relates to a guide catheter defining a substantially tubular delivery lumen through which one or more other functional catheters or devices may be introduced. The guide catheter may have one, or any combination of two or more, of the following features (which are all optional):

(i) The guide catheter may have a sufficient length to extend from a site of a skin incision, along a vasal route of the vasculature, to a position in the ascending aorta.

(ii) The guide catheter may serve as a single guide for the introduction of one or more other functional catheters or devices therethrough during the procedure, while the guide catheter remains in situ.

The presence of a single guide catheter through which such other catheters and/or devices may be introduced, can reduce the risk of direct abutment and/or abrasive rubbing contact between the vasculature wall and each catheter/device being introduced or removed. This may be especially advantageous in the aortic arch, which may suffer from the double problem of heavy calcification and bending through 180 degrees, and inevitably involving contact with the vassal wall. Instead, the guide catheter acts as a sheath that can protect, at least to some extent, the vasculature wall. There may be only a single introduction stage, and a single removal stage, involving the guide-catheter itself, independent of the number of other devices/catheters introduced and removed via the guide catheter. Furthermore, use of a protective guide-catheter may reduce the severe atraumatic design constraints normally associated with devices that have to be introduced via the vasculature (for example, atraumatic distal tips that occupy significant space, and require significant penetration into the interior of the ventricle).

Optionally, the guide catheter may comprise one or more blood-communication openings along its length to allow blood flood between the exterior and exterior of the guide catheter, and for example, allow for pressure equalization between the interior and exterior as a functional catheter/device is advanced or withdrawn within the interior of the guide catheter.

(iii) The guide catheter may be of, or comprise, flexible material that permits the lumen of the guide catheter to (i) collapse in cross-section to adopt a compact form for introduction into the vasculature, and/or (ii) distend in cross-section to accommodate the size of a functional catheter or other device introduced therethrough.

Collapsing to a small size can (i) simplify introduction through the incision through the skin and into the artery, (ii) enable a smaller incision to be used, for improved patient comfort and easier closing post-procedure, (iii) facilitate navigation along the vasculature to the ascending artery, even in cases of severe stenosis or tortuous vasculature, (iv) reduce risk of trauma and other abrasive rubbing against the vascular walls during introduction and later removal, and so reduce risk of damage to the vascular walls or dislodging calcification into the blood stream.

In some embodiments, the guide catheter may be introduced with a collapsed size that is smaller than, for example, a delivery catheter for implanting a prosthetic valve.

Optionally, the guide catheter is biased towards the relatively collapsed state, such that the guide catheter tends to return towards the relatively collapsed state when possible. Additionally or alternatively, a removable sheath may be used to constrain the guide catheter in the compact form.

In some embodiments, the wall of the guide catheter comprises sufficient material that the catheter can adopt the distended state without significant stretching of the material. The collapsed state is achieved by folding, pleating or corrugating of the material around the axis of the guide catheter. The distended state is achieved by the material unfolding. Using folding/unfolding of material to transition from the collapsed state to the distended state, can reduce significantly the friction exerted on a device being introduced through the guide catheter, compared to a similar catheter using elastic stretching to adopt a distended state.

In some embodiments, the wall of the guide catheter comprises an integral extrusion, for example, a plastics extrusion. The wall may be extruded in its relatively collapsed state. Alternatively, the wall may be extruded in a larger state, for example, the distended state or an intermediate state between the two. The wall may be "set" and/or biased to a smaller state, for example, by thermal shaping.

In some embodiments, the guide catheter is in the form of a braid or other meshed filament structure. Such a structure may also permit distension without substantial stretching of the material of the filaments.

(iii) The guide catheter may include an aligner operative to align at least a portion of a distal region of the guide catheter with respect to the native vasculature. The aligner may be part of the structure of the guide catheter. The aligner may function to align the position of at least a portion of the distal region of the guide catheter in register with a central region of the ascending aorta.

By aligning the position of the distal region of the guide catheter, other devices or catheters introduced through the guide catheter can be positioned or aligned reliably towards the centre of the existing valve at the implantation site. Such alignment provides significant advantages in ease of traversing the existing valve (especially a heavily calcified valve), and reliable positioning and/or alignment of a prosthetic valve for implantation.

The aligner may comprise one or more elements that, in an operative configuration, are arranged to expand towards and/or abut the wall of the vasculature, for example, the wall of the ascending aorta. The or each element may act as fender to space the guide catheter from the vasculature wall. In some embodiments, the or each element may comprise a wire, filament, flap, cantilever, lattice or a skeletal structure. The element may, for example, change shape controllably in response to application of compressive or tension stress. In other embodiments, the or each element may be inflatable, for example an inflatable balloon or cuff, responsive to introduction of inflation fluid (e.g., gas or liquid as preferred). In other embodiments, the aligner is part of the wall of the guide catheter that defines the delivery lumen. For example, the aligner may be a bulbous portion of the wall (especially if the wall is formed as a braid or other meshed filament structure).

Whichever kind of aligner may be used, it is preferred that the aligner be configured not to occlude substantially the vasculature, and to allow blood flow therethrough or therearound.

In some embodiments, the aligner may be configured to provide (e.g., controllable) alignment of the inclination of the longitudinal axis of the distal region of the guide catheter, in addition to mere positioning of a portion of the distal region. For example, the longitudinal axis of the guide catheter may be aligned substantially in register with or parallel to the axis of the ascending aorta, or the guide catheter axis may be inclined controllably to achieve a desired relation with respect to an existing valve of valve annulus. The angle of inclination of the guide catheter axis may be aligned and/or controlled by providing contact between the aligner and the vassal wall at spaced longitudinal positions. For example, the aligner may have an axially elongate contact profile. Additionally or alternatively, a first aligner element (or group of elements) may be arranged at a first longitudinal position, and a second aligner element (or group of elements) may be arranged at a second longitudinal position spaced with respect to the first position. For ease of control via respective lumen within the guide catheter, the first and second elements (or respective groups) may be offset angularly with respect to each other.

(iv) The guide catheter may comprise a filter deployable to capture debris that might in some cases be released into the blood stream during the TAVI procedure. The filter may, for example, comprise a net or grill.

If the guide catheter additionally comprises the aligner described above, it may be convenient for the filter to be carried by the aligner, such that the filter is deployed with the aligner. Optionally, the filter may also be stowed automatically when the aligner is placed in its non-operative configuration.

(v) The guide catheter may be configured to establish keyed engagement with a device or catheter introduced therethrough, in order to maintain the device/catheter in the same rotational orientation with respect to the guide catheter, while the device/catheter is advanced towards the distal region of the guide catheter.

In some embodiments, the keyed engagement may be defined by the cross-section shape of the guide catheter, for example, having a grooved, fluted, pleated or star shape.

(vi) The guide catheter may have, at or near its proximal end, a surrounding sleeve or sheath sealed to the wall of the guide catheter. The sleeve may have a generally smooth outer profile. The guide catheter may have a generally non-smooth outer profile (for example, a fluted, pleated or star shape as described above). The smooth surface of the sleeve may enable a better seal to be formed at the proximal end, to reduce the risk of blood leakage that might otherwise occur through the folds and pleats of a non-smooth outer profile.

(vii) The guide catheter may comprise, at least initially for introduction into the vasculature and advancement to the ascending aorta, a tapered or rounded tip device at the distal region. The tip may optionally be openable and/or separable from the guide catheter.

Broadly speaking, a second aspect of the invention provides, in combination, a guide catheter as aforesaid, and a dilation catheter and/or a delivery catheter. The dilation catheter and/or delivery catheter may be insertable through the guide catheter. The catheters may, for example, be provided together as a kit.

Broadly speaking, a third aspect of the invention provides apparatus for aligning, within the ascending aorta, a transvascular delivery catheter for delivering a prosthetic valve to an implantation site, the assembly comprising at least one aligner element movable from a non-operative configuration in which the aligner element does not protrude substantially, to an operative configuration in which the aligner protrudes outwardly towards and/or for abutting, the wall of the ascending aorta. The alignment apparatus may be an integral part of the delivery catheter, or it may a supplementary apparatus fitable to the delivery catheter, or within which the delivery catheter may be received. The aligner may be distinct from self-alignment features of an implantable stent carried by the delivery catheter. The aligner may be significantly advantageous in enabling the position and/or inclination of the delivery catheter to be aligned at or near the implantation site, which in turn may aid implantation of the prosthetic valve.

Broadly speaking, a fourth aspect of the invention provides a method for use in a transcatheter aortic valve implantation process, the method comprising:

introducing a distal region of a guide catheter into the vasculature, the guide catheter having a tubular delivery lumen, and advancing the guide catheter such that the distal portion of the guide catheter is placed within the ascending aorta.

The method may optionally further comprise one, or a combination of any two or more, of following steps. The order of the steps may be varied as desired, and is not limited by the order of description:
(a) Removing a sheath constraining the guide catheter to a collapsed shape, thereby to permit distension of the guide catheter;
(b) Separating a tip from the distal region of the guide catheter, and withdrawing the tip, optionally via the delivery lumen of the guide catheter;
(c) Introducing a dilation catheter via the delivery lumen of the guide catheter, to a site for, or of, implantation.
(d) Introducing a stent-valve delivery catheter via the delivery lumen of the guide catheter to the site of implantation.
(e) Deploying and/or controlling an aligner at a distal region of the guide catheter to align the position of at least a portion of the distal region with respect to the ascending aorta. The step of deploying and/or controlling may align the position of at least a portion of the distal region of the guide catheter with respect to a central region of the ascending aorta, for example, with respect to a central axis. In some embodiments, the step of deploying and/or controlling comprises aligning an angle of inclination of the longitudinal axis of the distal region with respect to the ascending aorta.

The step (e) may be carried out prior to steps (c) and/or (d) above. Additionally, the step (e) may be carried out during the steps (c) and/or (d) above, to accommodate and/or compensate for potential distension of the distal region of the guide catheter as a dilation catheter and/or a delivery catheter is passed therethrough.

(f) Placing the aligner in a non-deployed or non-operative configuration after use.
(g) Determining a rotational orientation of the distal region of the guide catheter in the ascending aorta.
(h) Introducing a delivery catheter at a proximal end of the guide catheter, the guide catheter being orientated rotationally with respect to the proximal end of the guide catheter in order to be advanced to the distal region of the guide catheter with a desired rotational orientation with respect to the ascending aorta.
(i) deploying a filter to capture any debris introduced into the blood stream by the implantation procedure.

Broadly speaking a fifth aspect of the present invention provides a method of operating a delivery catheter for transcatheter aortic valve implantation, the method comprising:
(a) introducing a distal region of the deliver catheter to a site for implantation, via a transvascular access route reaching to and/or through the ascending aorta;
(b) operating an aligner at or adjacent to the distal region of the delivery catheter for aligning a position and/or inclination of the distal region with respect to the ascending aorta;
(c) operating the delivery catheter to implant the prosthetic valve at the implantation site.

In a further aspect, the invention provides a guide catheter for introduction into a patient's vasculature, to provide a substantially continuous guide lumen within the vasculature to the ascending aorta, through which one or more other functional catheters may be introduced and removed during a transcatheter aortic valve implantation procedure. The guide catheter optionally includes an aligner at its distal region for aligning the position and/or inclination of the distal region of the guide catheter with respect to the ascending aorta. The aligner optionally includes an embolic protection filter. The guide catheter optionally is made of material collapsible/distensible in cross section to adopt a small shape when no catheter is present inside, and to distend to a large shape to accommodate passage of functional catheter therethrough. The cross-section shape may collapse/distend by folding/unfolding of material without elastic stretching of the material.

Further aspects, features and advantages of the invention will become apparent from the following description, claims and drawings. The Applicant claims independent protection for any novel feature, combination of features, or idea, that is described herein and/or illustrated in the drawings, whether or not emphasis has been placed thereon.

DETAILED DESCRIPTION OF THE INVENTION AND PREFERRED EMBODIMENTS

Where appropriate, the same reference numerals are used to denote equivalent features in various different embodiments.

Figure 1:
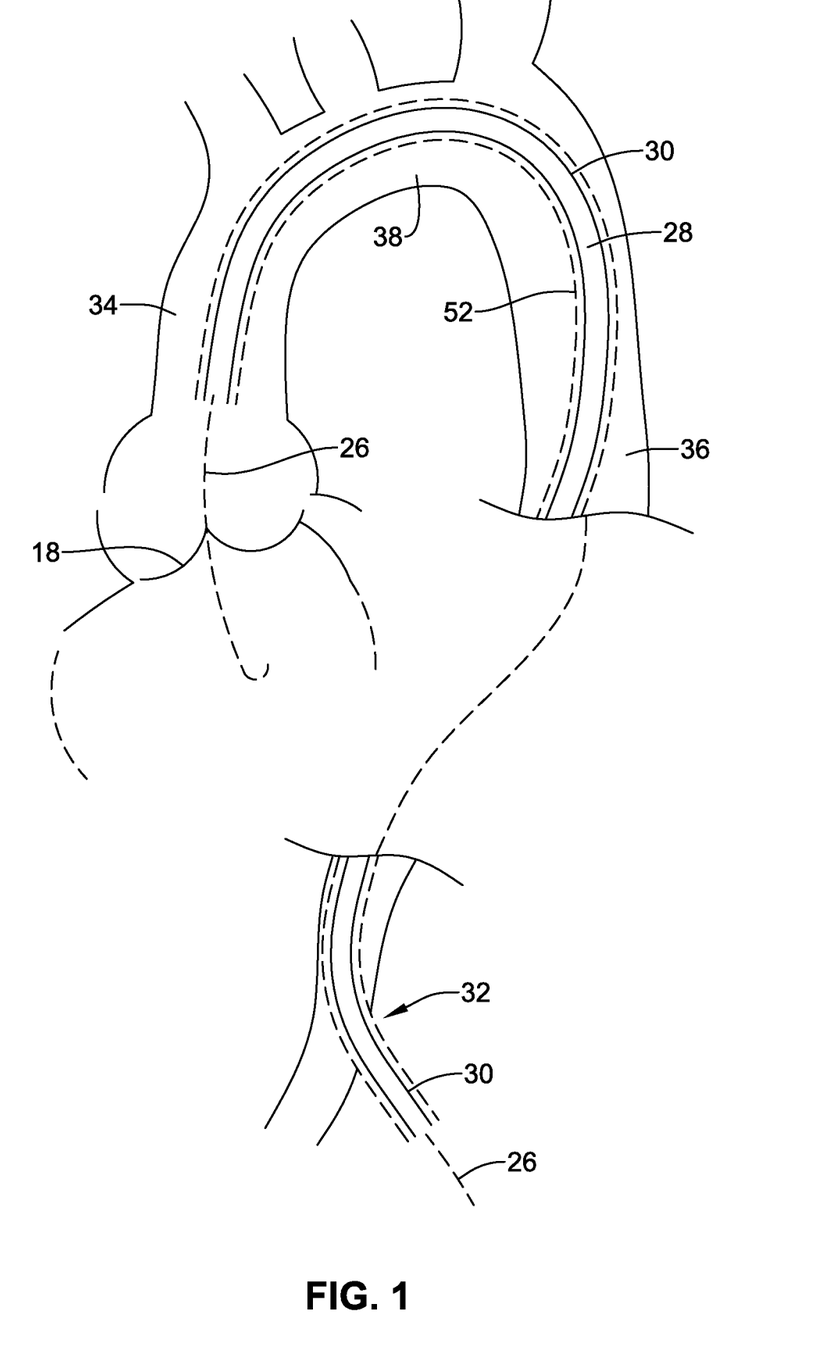
FIG. 1 is a schematic section illustrating a guide catheter introduced into the anatomy via a vascular approach and extending to the ascending aorta.
Figure 2:
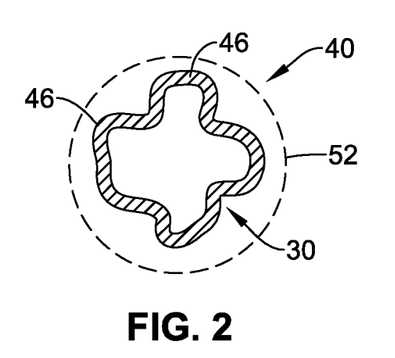
FIG. 2 is a schematic cross-section through one example of the guide catheter in isolation, in a collapsed state.

Broadly speaking, one aspect of the present invention relates to a guide catheter 30 defining a substantially tubular delivery lumen 28 through which one or more other functional catheters or devices may be introduced. In various preferred embodiments, the guide catheter 30 may have one, or any combination of two or more, of the following features (which are all optional):

(i) Referring to FIG. 1, the guide catheter 30 may have a sufficient length to extend from a site of a skin incision 32, along a vassal route of the vasculature to a position in the ascending aorta 34. For a transfemoral approach, the guide catheter may have a sufficient length to extend from an incision 32 into the femoral artery, along the descending aorta 36, the aortic arch 38 to the ascending aorta 34. For example, a transfemoral guide catheter may have a length of at least 100 cm (preferably at least 110 cm, optionally at least 115 cm).

With such an arrangement, the guide catheter 30 can provide a substantially continuous guide path within the vasculature from the site of incision 32 to a position within the ascending aorta 34 adjacent to a desired implantation site.

(ii) The guide catheter 30 may serve as a single guide for the introduction of one or more other catheters or devices therethrough during the procedure, while the guide catheter 30 remains in situ. For example, the guide catheter 30 may serve for the introduction of a dilation catheter (not shown) for performing pre-implantation dilation of the existing valve 18 (e.g. valvuloplasty of a native valve, or dilation of an existing malfunctioning prosthetic valve). Pre-implantation dilation may be appropriate to "crack" open the existing valve leaflets which may often be cemented in a constricted or near-closed state by the presence of severe calcification. Additionally or alternatively, the guide catheter 30 may serve for the introduction of a delivery catheter (not shown) for delivering and implanting a prosthetic valve at the implantation site. Additionally or alternatively, the guide catheter 30 may serve for the introduction of a post-implantation dilation catheter that is sometimes appropriate to increase the size of the prosthetic valve unit after implantation (for example, to increase the valve aperture, enhance valve anchoring, and/or reduce paravalvular leakage). The presence of a single guide catheter 30 through which other functional catheters and/or devices may be introduced, can reduce the risk of direct abutment and/or abrasive sliding contact between the vasculature wall and each functional catheter/device being introduced or removed. This may be especially advantageous in the aortic arch, which may suffer from the double problem of heavy calcification and bending through 180 degrees, and inevitably involving contact with the vassal wall. Instead, the guide catheter 30 acts as a sheath that can protect, at least to some extent, the vasculature wall. There may be only a single introduction stage, and a single removal stage, involving the guide-catheter 30 itself, independent of the number of other functional devices/catheters introduced and removed via the guide catheter 30. Furthermore, use of a protective guide-catheter 30 may reduce the severe atraumaticity/tracking design constraints normally associated with devices that have to be introduced via the vasculature. For example, a delivery catheter is normally required to have an atraumatic tip capable of tracking along a guidewire in the vasculature without rupturing the vassal wall. Additionally, a conventional delivery catheter should avoid any exposed edges or surface discontinuities that could catch or rub on the vassal wall, or abut on features of the vasculature. Additionally, a conventional delivery catheter should be sufficiently soft and compliant to facilitate tracking along the vasculature without damaging the vassal wall. The use of a guide catheter can reduce the severity of such constraints, and increase the design freedom. A further advantage is that, should a surgeon decide to use the same dilation catheter to perform both pre-implantation dilation and post-implantation dilation, there is considerably less risk to the patient. A conventional dilation catheter comprises a balloon that is tightly compressed prior to first use, but which is less compressed after initial dilation, and so has more risk of rubbing against and catching on the vassal wall if introduced a second time for post-implantation dilation. The use of a guide catheter can prevent or at least reduce risk of rubbing/catching of the balloon material against the vassal wall even if the same dilation catheter is used a second time.

In some embodiments, the guide catheter may comprise one or more blood-communication openings (54 in FIG. 1)

along its length to allow blood flood between the exterior and exterior of the guide catheter, and for example, allow for pressure equalization between the interior and exterior as a functional catheter/device is advanced or withdrawn within the interior of the guide catheter. If the wall of the guide catheter is generally continuous, the openings 54 may have the form of discrete windows or apertures formed in the wall. Alternatively, the openings may be formed by open space in, for example, a mesh structure defining the guide catheter.

Figure 3:
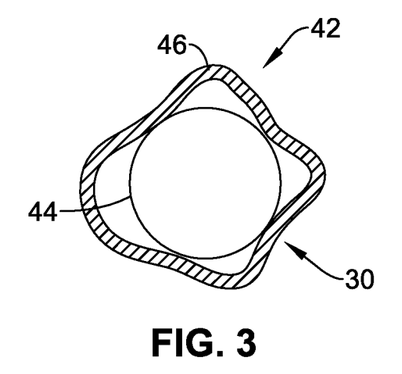
FIG. 3 is a schematic cross-section similar to FIG. 2, but showing the guide catheter in a distended state.
Figure 4:
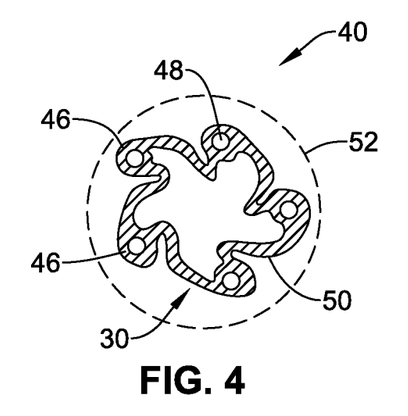
FIG. 4 is a schematic cross-section through a second example of the guide catheter in isolation, in a collapsed state.
Figure 5:
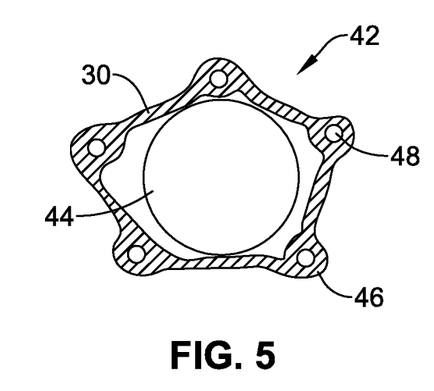
FIG. 5 is a schematic cross-section similar to FIG. 4, but showing the guide catheter in a distended state.
Figure 6:
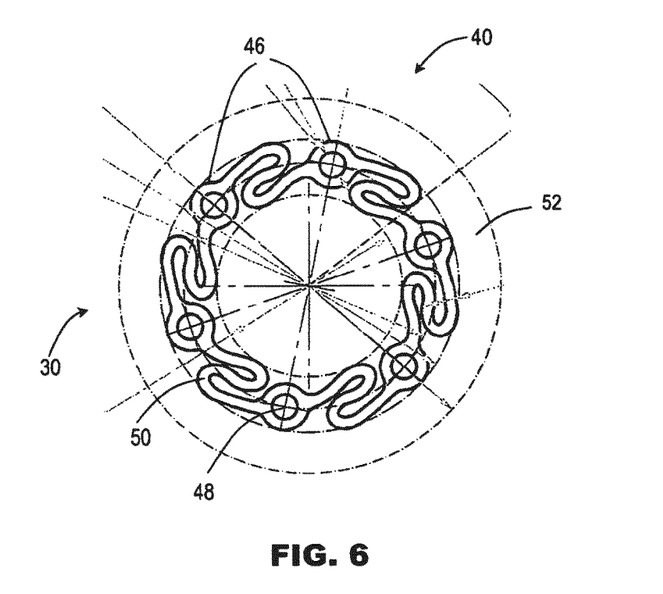
FIG. 6 is a schematic cross-section through a third example of the guide catheter in isolation, in a collapsed state.
Figure 7:
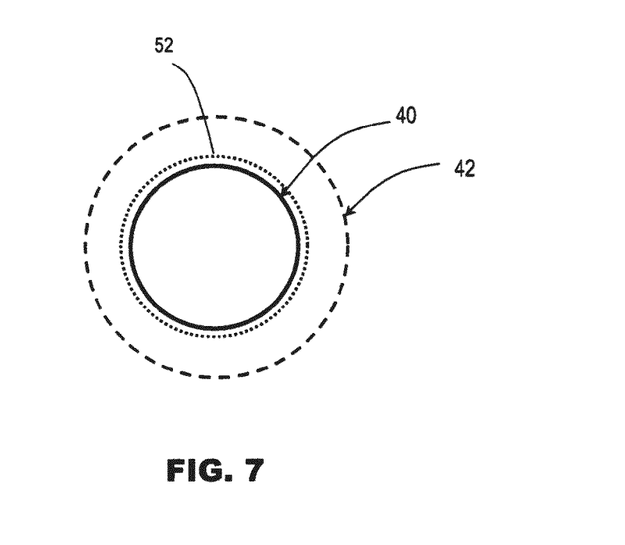
FIG. 7 is a schematic cross-section through a fourth example of the guide catheter in isolation, showing the collapsed state and in broken-line the distended state.

(iii) Referring to FIGS. 2-7, the guide catheter 30 may be of, or comprise, flexible material that permits the guide catheter to (i) collapse in cross-section to a compact form 40 (e.g. as illustrated in FIGS. 2, 4, 6 and 7) for introduction into the vasculature, and (ii) distend in cross-section to a distended form 42 to accommodate the size of a functional catheter (shown schematically at 44) introduced therethrough (e.g. as illustrated in FIGS. 3, 5 and 7). The compact form 40 may, for example, correspond to an outer diameter less than about 6 mm (18 French), for example about or less than 5.3 mm (16 French), or about or less than 4.7 mm (14 French), or about or less than 4 mm (12 French). The distended form 42 may be large enough to provide an inner diameter size of at least about 6 mm (18 French), for example at least about 6.7 mm (20 French), or at least about 7.3 mm (22 French), or at least about 8 mm (24 French). Such an arrangement can enable the guide catheter 30 to have a collapsed size that is smaller than a typical delivery catheter 40 (typically having an outer diameter in the range of 6-8 mm). A small size can (i) simplify introduction through the incision 32 through the skin and into the artery, (ii) enable a smaller incision 32 to be used, for improved patient comfort and easier closing post-procedure, (iii) facilitate easier navigation along the vasculature to the ascending artery 32, even in cases of severe stenosis or tortuous vasculature, (iv) reduce risk of trauma and other abrasive rubbing against the vascular walls during introduction and later removal, and so reduce risk of damage to the vascular walls or dislodging calcification into the blood stream.

In some embodiments, the wall of the guide catheter 30 comprises sufficient material that the catheter 30 can adopt the distended state 42 without significant stretching of the material. In some embodiments (FIGS. 2, 4 and 6), the collapsed state 40 is achieved by folding, pleating or corrugating the material in a peripheral or circumferential direction, e.g., around the axis of the guide catheter. The distended state 42 is achieved by the material unfolding. Using folding/unfolding of material to transition from the collapsed state to the distended state, can reduce significantly the friction exerted on a device being introduced through the guide catheter, compared to a similar catheter using elastic stretching of the material to adopt a distended state. For example, in the collapsed state (FIGS. 2, 4 and 6), the material may fold to a generally pleated or fluted shape (also referred to herein as a star cross-section) or to an annular shape with S-folds. The apexes 46 of the cross-sectional shape may, in some embodiments (FIGS. 4 and 6) comprise one or more tubular portions defining lumen 48 (e.g. for controlling the distal region of the guide catheter as optionally described later, and/or for introducing contrast medium to the distal region). The design shown in FIGS. 4 and 6 also illustrates the folding of the material segments 50 between apexes 46 being asymmetric compared to a radial direction. Such asymmetric folding may enable a large circumferential length of material to be accommodated within each segment 50. The asymmetric folding may also encourage a more compact form, by the material segments 50 being partially rolled-up when in the collapsed state 40.

FIG. 7 illustrates an alternative round cross-section shape suitable for a braid or other woven material. Such material has the ability to permit distension of the cross-section shape by rearrangement of the filaments in the woven structure, without substantial elastic stretching extension of the filaments themselves.

The guide catheter 30 may be made of any suitable biocompatible material, including by way of example only, silicone, polyether block amide (e.g., "Pebax"®), or a metal braid, for example, of stainless steel or nitinol. The shapes of FIGS. 2-5 may be produced by plastics extrusion, or may be shaped from metal braids. The shape of FIG. 7 may be appropriate for a metal braid.

In some embodiments, the guide catheter 30 is self-biased towards the collapsed state 40, or at least to an intermediate partly collapsed/partly distended state that is smaller than the fully distended state 42. This can help reduce occlusion of the vasculature occupied by the guide catheter 30.

In some embodiments, self-biasing is achieved by extruding the plastics wall in its collapsed state 40. In some other embodiments, self-biasing is achieved by extruding the plastics wall in a larger state (for example, the fully distended state 46), and setting or biasing the material to a smaller state using, for example, thermal shaping.

Figure 12:
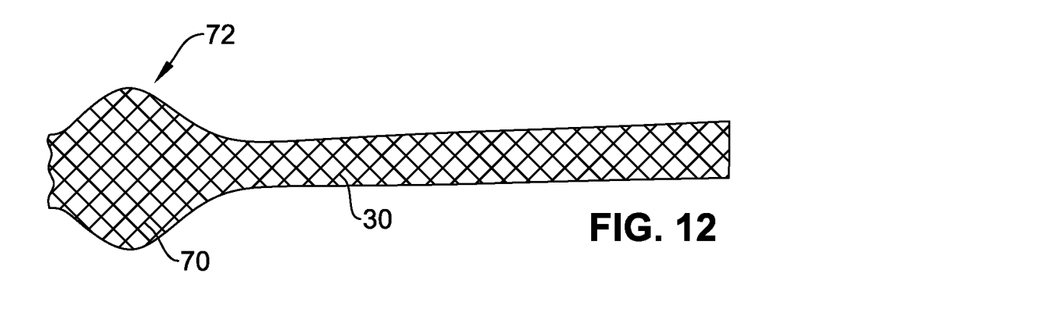
FIG. 12 is a schematic side view of a further example of guide catheter forming of braiding.
Figure 13:
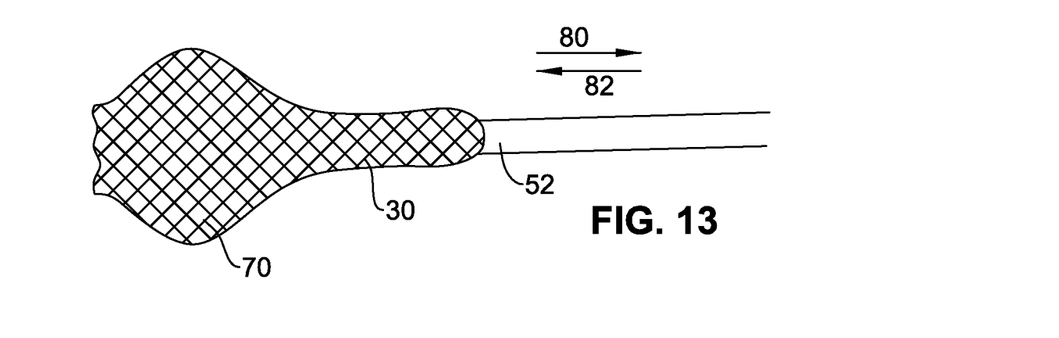
FIG. 13 is a schematic side view illustrating sheathing and unsheathing of the braiding.
Figure 14:
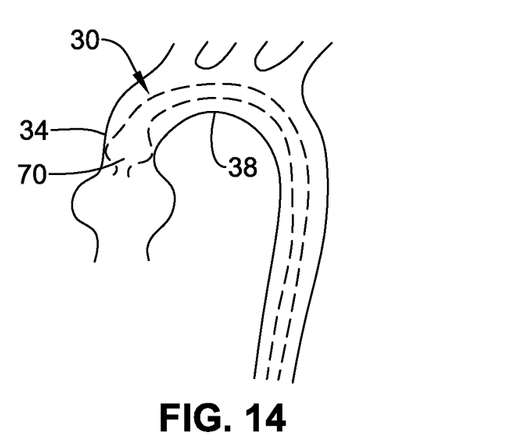
FIG. 14 is a schematic cross-section illustrating positioning of the guide catheter of FIG. 13 in the anatomy.

In some embodiments, the guide catheter 30 may initially be contained within and/or constrained by a displaceable sheath 52 (shown in phantom in FIG. 1; in phantom around the collapsed state 40 in FIGS. 2, 4, 6 and 7; and in FIGS. 12 and 14). The sheath 52 may optionally constrain the guide catheter 30 in its collapsed form 40 for ease of introduction into the vasculature. The sheath 52 may be withdrawn proximally to remove it from the guide catheter 30 after introduction of the guide catheter 30 into the vasculature, or reaching the ascending aorta 34.

(iv) Referring to FIGS. 8-17, the guide catheter 30 may include an aligner 70 operative to align at least a portion of a distal region 72 of the guide catheter with respect to the native vasculature. The aligner 70 may be part of the structure of the guide catheter 30. The aligner 70 may function to align the position of at least a portion of the distal region 72 of the guide catheter in register with a central region of the ascending aorta 34, for example, substantially in register with a centre point or axis of the ascending aorta 34. By aligning the position of the distal region 72 of the guide catheter, other functional devices or catheters (indicated schematically at 44) introduced through the guide catheter can be better positioned or directed reliably through the centre of the existing valve 18 at the implantation site. This can be achieved even if the functional device or catheter has no active bending or steering ability of its own, enabling the distal portion of the functional catheter to be simplified or made more compact compared to a functional catheter with remote steering or bending actuators incorporated at its distal end. The alignment provided by the aligner 70 can provide significant advantages in ease of traversing the existing valve 18 (especially a heavily calcified valve), and reliable positioning and/or alignment of a prosthetic valve for implantation.

In some embodiments, the aligner 70 is movable between a non-operative (e.g. stowed) configuration (shown in FIGS. 10 and 12; in phantom in FIGS. 9 and 13) and an operative (e.g. deployed) configuration (shown in FIGS. 8, 9, 11 and 13-17). In the non-operative configuration, the aligner may be stowed so that it is relatively collapsed and/or retracted and/or streamlined with the shape of the guide catheter 30, to facilitate introduction and removal of the guide catheter 30 with respect to the vasculature. In the operative configuration, the aligner may be deployed to expand towards and/or about the wall of the vasculature, for example, the wall of the ascending aorta 34. The aligner 70 may act as fender to space the guide catheter 30 (or at least the delivery lumen 28 thereof) from the vasculature wall.

In some embodiments, the aligner 70 is biased to one of the operative and non-operative configurations, and the aligner 70 is movable to the other configuration by a reversible manual perturbation effect applied thereto from the proximal end or portion of the guide catheter 30.

Figure 9:
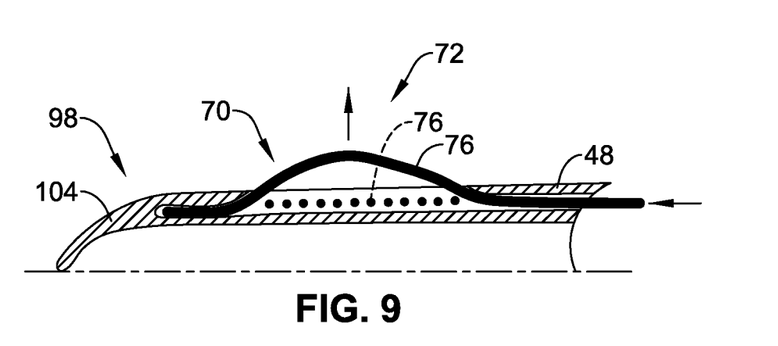
FIG. 9 is a schematic cross-section showing one example of aligner formed of aligner elements.
Figures 10, 11:
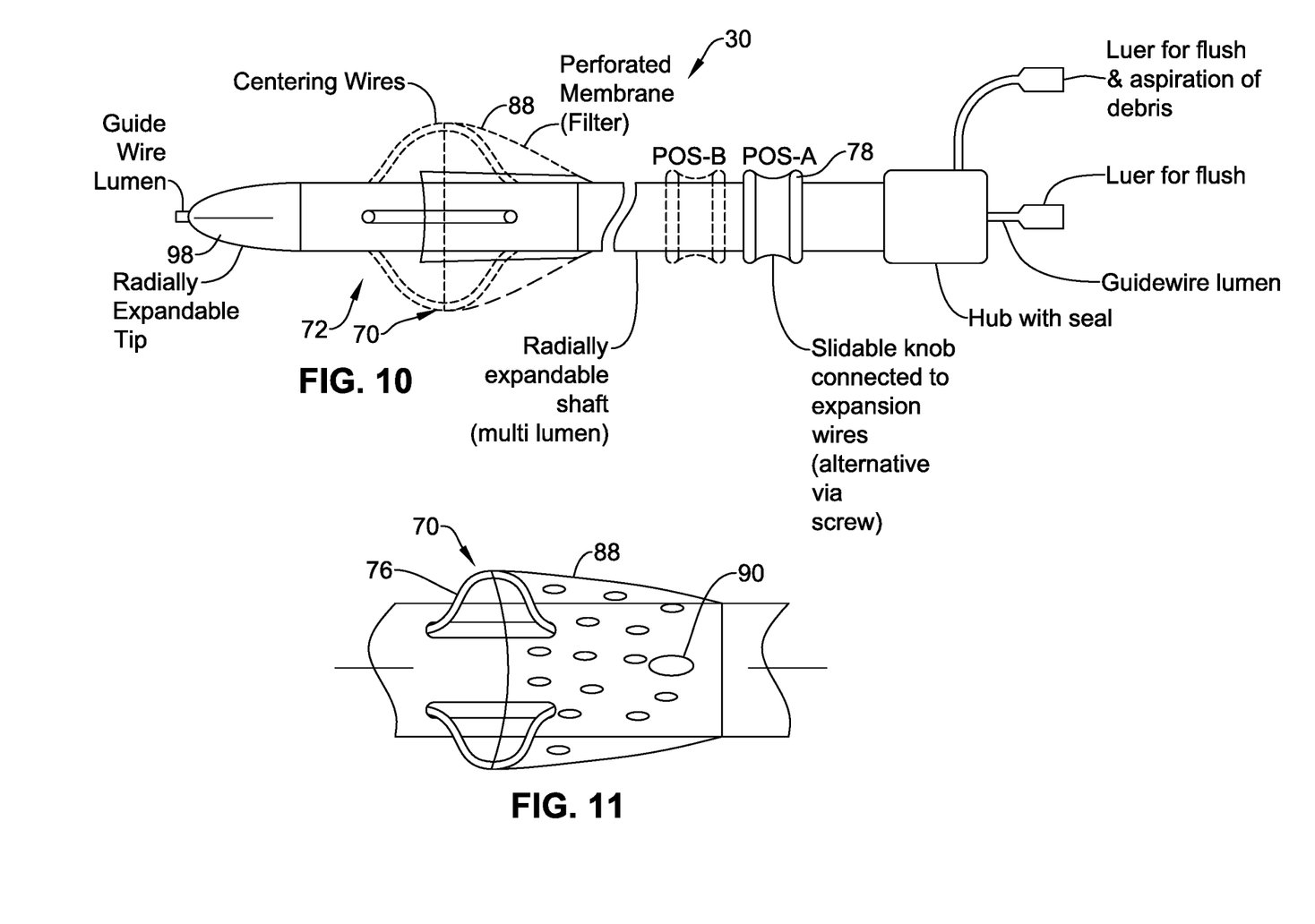
FIG. 10 is a schematic side-view showing the guide catheter of FIG. 8 in isolation.
FIG. 11 is a schematic side view showing the aligner, filter and aspiration apertures of the guide catheter in more detail.

In some embodiments (FIGS. 8-11), the aligner 70 comprises one or more (and preferably a plurality of) elements 76 that, in the operative configuration, are arranged to expand or project outwardly with respect to the wall of the guide catheter 30 (indicated by the broken line 30' in FIG. 11). For example, at least one of the elements 76 may comprise a wire, filament, flap, cantilever, lattice or a skeletal structure. The element 76 may, for example, change shape controllably in response to application of tension or compression stress, for example, applied from the proximal end of the guide catheter 30. In some embodiments, the one or more elements 76 are formed by wires that extend substantially the length of the guide catheter. For example, the wires may extend within the lumen 48. The wires are substantially captive, or constrained within the lumen 48 over the majority of the length, but are partly exposed at the distal region 72, at which the wires may expand or buckle to project outwardly to define the aligner elements 76. The distal ends of the wires are received again within the lumen 48, and may optionally be sealed or captively held. In some embodiments, the wires may be biased to a collapsed, non-operative configuration, but may be distended to the operative configuration by reversible application of stress from the proximal end. The proximal end may comprise one or more controls 78 for applying such stress. Alternatively, the wires may be biased to a distended, operative configuration and may be constrainable in a collapsed, non-operative configuration by reversible movement of a constraining sheath, such as or similar to the sheath 52 described earlier. The constraining sheath may be withdrawn from the proximal end of the guide catheter after introduction of the guide catheter 30 into the vasculature, or reaching the ascending aorta 34.

Preferably, the aligner comprises at least three aligner elements 76 arranged around the circumference of the guide catheter 30 at the distal region 72. The aligner elements 76 may optionally be equally angularly spaced.

In other embodiments, at least one of the elements 76 may be inflatable, for example an inflatable balloon or cuff, responsive to introduction of inflation fluid (e.g., gas or liquid as preferred).

Figure 15:
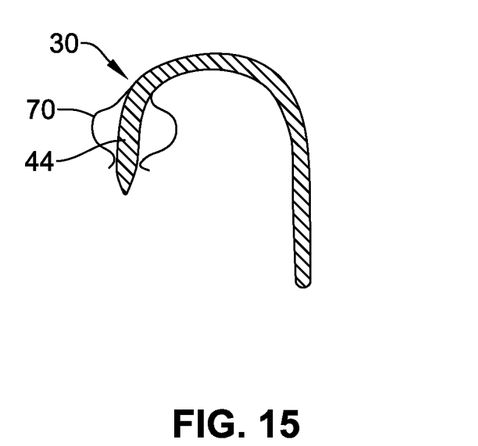
FIG. 15 is a schematic cross-section illustrating introduction of a functional catheter through the guide catheter of FIG. 14 (shown in isolation for ease of view).
Figure 16:
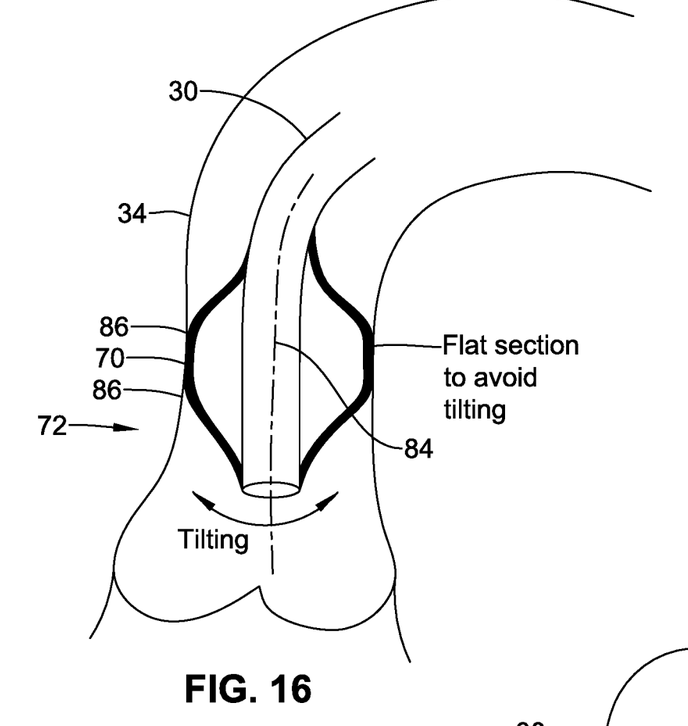
FIG. 16 is a schematic section showing a modified profile of aligner for aiding alignment of the guide catheter axis.
Figure 17:
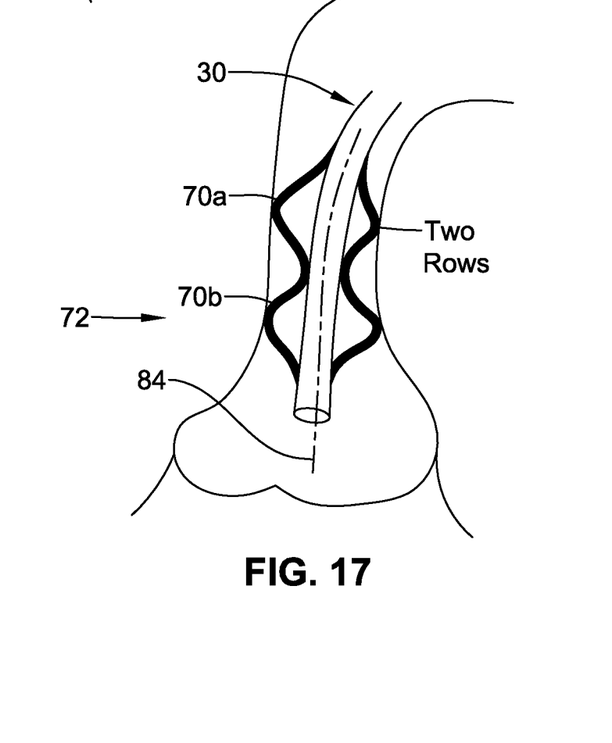
FIG. 17 is a schematic section similar to FIG. 16, but showing a second modified form of aligner.

In other embodiments (FIGS. 12-15), the aligner 70 is formed by expansion or swelling of a portion of the tubular wall of the guide catheter 30 (as indicated by the full line in FIG. 15. For example, the guide catheter 30 may be formed as a braid, the distal portion 72 of which is self-biased (for example, by suitable heat treatment or other training) towards a bulged or bulbous shape defining the aligner 70. The aligner 70 may be constrainable in a collapsed, non-operative configuration by reversible movement of a constraining sheath, such as or similar to the sheath 52 described earlier. The constraining sheath may be withdrawn from the proximal end of the guide catheter (in the direction indicated by arrow 80 in FIG. 13) after introduction of the guide catheter 30 into the vasculature, or reaching the ascending aorta 34. As the sheath 52 is withdrawn, the aligner 70 swells to its operative configuration (FIG. 14). A functional catheter 44 may be introduced through the guide catheter 30 as described previously (FIG. 15). When it is desired to remove the guide catheter 30, the sheath 50 is repositioned by advancing over the length of the catheter 30 from the proximal end (in the direction indicated by arrow 82 in FIG. 13), in order to re-collapse the aligner 70 to its non-operative configuration.

Whichever kind of aligner 70 may be used, it may be preferred that the aligner 70 be configured not to occlude substantially the vasculature, and to allow blood flow therethrough or there-around.

Various profile shapes of aligner 70 are envisaged. The aligner 70 is preferably configured to define a relatively atraumatic contact surface with the vassal wall. For example, the aligner may have a rounded or blunt profile shape.

In some embodiments (e.g. FIGS. 16 and 17), the aligner 70 may be configured to provide (e.g., controllable) alignment of the inclination of the longitudinal axis 84 of the distal region 72 of the guide catheter 30, in addition to mere positioning of a portion of the distal region 72. For example, the longitudinal axis 84 of the guide catheter 30 may be aligned substantially in register with or parallel to the axis of the ascending aorta 34, or the guide catheter axis may be inclined controllably to achieve a desired relation with respect to an existing valve annulus. In one form illustrated in FIG. 16, the angle of inclination is controlled by shaping the aligner 70 to define elongate contact with the aorta wall, or at least contact at or between first and second axially spaced points 86. In an alternative form illustrated in FIG. 17, the angle of inclination of the guide catheter axis 84 may be aligned and/or controlled by providing aligner portions 70a and 70b at plural longitudinal positions at the distal portion 72. For example, a first aligner portion 70a may be arranged at a first longitudinal position, and a second aligner portion 70b may be arranged at a second longitudinal position spaced with respect to the first position. For ease of control via respective lumen within the guide catheter, the first and second aligner portions 70a and 70b (or respective groups) may be offset angularly with respect to each other.

In some embodiments, control is provided for manipulating plural elements 76 of the aligner 70 in unison. For example, FIG. 10 illustrates a control 78 coupled to plural wires 76. Additionally or alternatively, a group of plural elements may be manipulated in unison independently of at least one other element or group. For example, this may be useful to controlling the inclination of the distal portion of the guide catheter as explained above. Additionally or alternatively, one or more of the elements may be manipulated independently. For example, this may be useful for fine tuning the position and/or inclination of the distal portion of the guide catheter. It might also be useful for identifying or verifying the rotational orientation of the guide catheter within the ascending aorta.

By manipulating a specific element while observing the catheter in situ using standard medical imaging apparatus, the rotational orientation of the distal portion can be identified.

In some embodiments, the aligner is movable to a non-operative configuration in which the aligner is retracted or collapsed towards the guide-catheter. In the non-operative position, the aligner has a more streamlined shape, suitable for introduction and removal of the guide catheter with respect to the vasculature.

Figure 8:
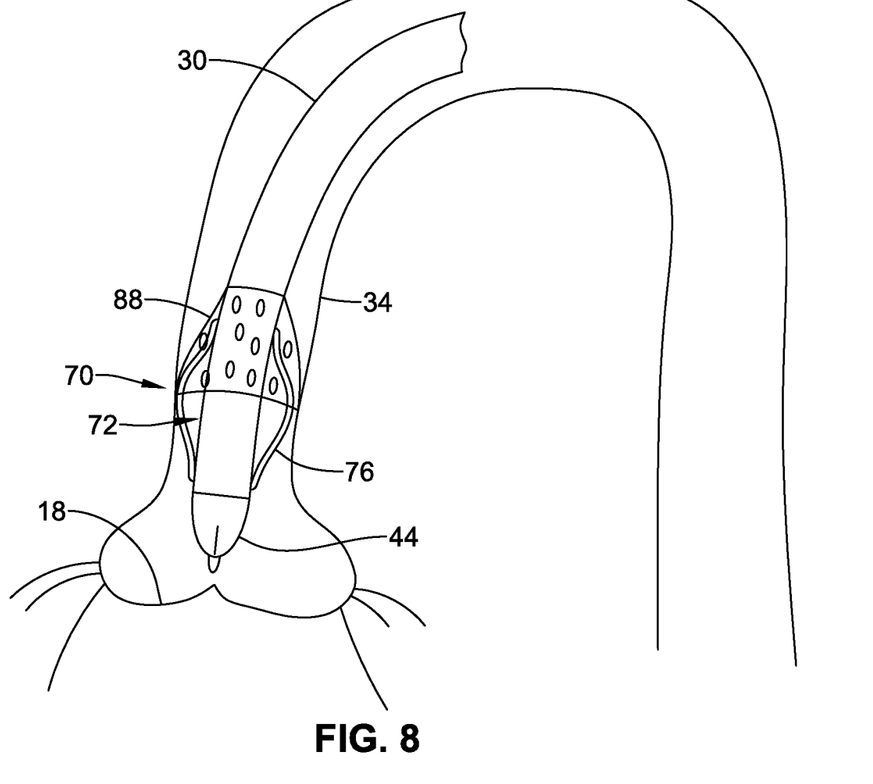
FIG. 8 is a schematic cross-section illustrating a guide catheter introduced into the anatomy and having an aligner shown in the operative position.

(iv) Referring to FIGS. 8, 10 and 11, the guide catheter 30 may comprise a filter 88 deployable to capture debris that might in some cases be released into the blood stream during the TAVI procedure. The filter 88 may, for example, comprise a net, grill or an apertured sheet.

If the guide catheter 30 additionally comprises the aligner 70 described above, it may be convenient for the filter 88 to be carried by the aligner 70, such that the filter 88 is deployed in unison with the aligner 70. Optionally, the filter 88 may also be stowed automatically when the aligner 70 is placed in its non-operative configuration.

The distal portion 72 of the guide catheter 30 may optionally further comprise one or more aspiration apertures 90 (FIGS. 10 and 11), communicating with the proximal portion of the guide catheter 30, through which collected debris may be aspirated.

Figure 18:
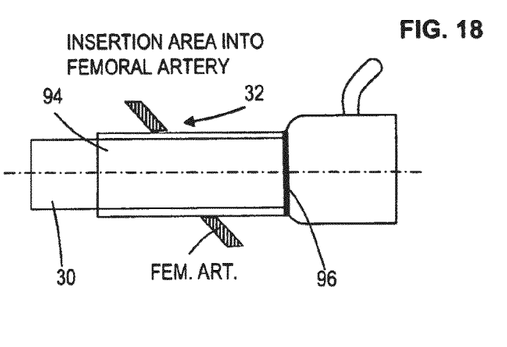
FIG. 18 is a schematic side-view illustrating a sleeve at a proximal end of the guide catheter.
Figure 19:
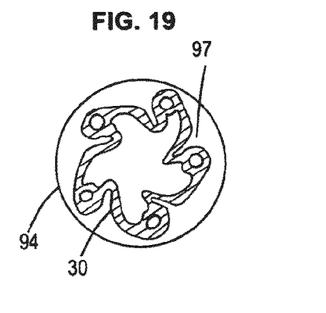
FIG. 19 is a schematic cross-section through the proximal end of the guide catheter showing the sleeve of FIG. 18.

(v) Referring to FIGS. 18 and 19, the guide catheter 30 may have, at or near its proximal end, a surrounding sleeve 94 sealed at 96 to the wall of the guide catheter 30. The sleeve 94 may have a generally smooth outer profile. The sleeve 94 may be elastically stretchable (e.g. to accommodate expansion of the guide catheter 30 when a functional catheter is introduced therethrough). The guide catheter 30 may have a generally non-smooth outer profile (for example, a fluted, pleated or star shape as described above and illustrated in FIG. 19). The smooth surface of the sleeve 94 may enable a better seal to be formed at the proximal end, to reduce the risk of blood leakage that might otherwise occur through the folds and pleats 97 of a non-smooth outer profile. The length of the sleeve 94 may be sufficient to ensure that the sleeve 94 is received partly within the vasculature at the site of the skin incision 32 (FIG. 18). For example, the sleeve 94 may extend a distance of at least 20 mm from the proximal end, towards the distal end.

(vi) The guide catheter 30 may be configured to establish keyed engagement with a functional device or catheter introduced therethrough, in order to maintain the functional device/catheter in the same rotational orientation with respect to the guide catheter, while the functional device/catheter is advanced towards the distal region of the guide catheter 30. If the rotational alignment of the distal region of the guide catheter 30 with respect to the native anatomy is known, this can enable the functional device/catheter guided by the guide catheter to be introduced with a predictable and reliable rotational orientation. Such a feature can avoid, or at least reduce, the burden of trying to rotate the catheter/device remotely from the proximal end once the catheter/device has arrived at or near the implantation site. Rotational orientation may be important, for example, for certain designs of prosthetic valve that are intended to be implanted with a certain rotational orientation with respect to the local anatomy. The rotational orientation of the distal end of the guide catheter may be identified or verified, for example, by imaging one or more indicia of the distal region, or by manipulating an aligner element as explained later.

In some embodiments, the keyed engagement may be defined by the cross-section shape of the guide catheter, for example, having a grooved, fluted, pleated or star shape as illustrated in FIGS. 2-6.

(vii) Referring to FIGS. 9, 10 and 20-23, the guide catheter 30 may comprise, at least initially for introduction into the vasculature and advancement to the ascending aorta, a tapered or rounded tip 98 at the distal end. The tip 98 may have a distally-facing tip surface defining an atraumatic shape designed to facilitate advancement of the distal region of the guide catheter 30 through the vasculature. The tip 98 may be made of soft and/or flexible plastics. The tip 98 may have a guide-wire receiving opening or lumen 100 allowing the guide catheter 30 to be advanced along a guide-wire 26.

Figure 20:
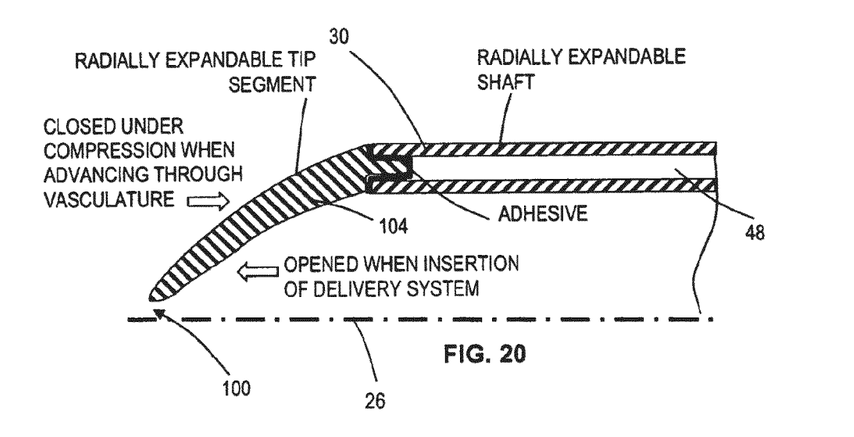
FIG. 20 is a schematic cross-section through a distal end of the guide catheter illustrating one example of tip.
Figure 21:
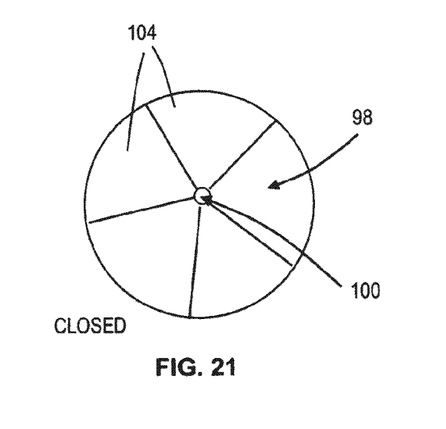
FIG. 21 is an end view of the distal end of the guide catheter of FIG. 20, showing the tip in the closed state.
Figure 22:
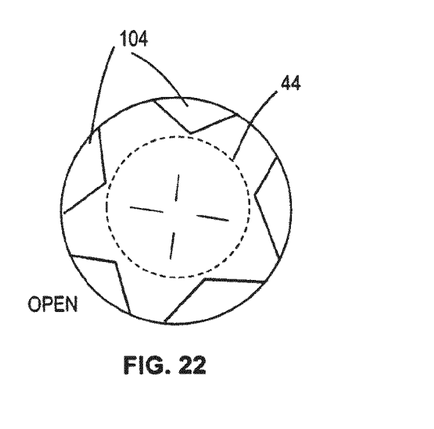
FIG. 22 is an end view of the distal end of the guide catheter similar to FIG. 21, but showing the tip in the open state.

In one form (e.g. as illustrated in FIGS. 20-22), the tip 98 comprises a plurality of segments or petals 104 capable of flexing movement. The petals may, for example, be generally triangular in shape. For example, the number of petals may be the same as the number of lumen 48, and the petals 104 may be mounted, one to each lumen 48 of the guide catheter. The petals 104 may be secured to the distal end of the guide catheter 30, for example, by an interference fit or by adhesive. (Alternatively, as illustrated in FIG. 9, each petal 104 may be an integral extension of the tubular wall of the guide wire 30). Each petal 104 is capable of flexing, for example, about a mounting or hinge point, and/or generally along its length. When the guide catheter 30 is advanced through the vasculature, the petals 104 adopt an inwardly directed shape (FIGS. 20 and 21), by virtue of blood pressure pressing on the exterior surface, and/or by the petals 104 having a natural resilient inward bias. In the compressed form, the petals 104 meet or overlap to define a substantially continuous conical or other tapered, rounded or flared surface, optionally with the guide wire aperture 100. The petals may also displace to an open configuration (FIG. 22), for example, under modest pressure, to permit passage through the tip of a functional catheter (shown schematically at 44).

In a slightly modified form, the petals 104 may be provided at the distal end of a cover sheath 52. The petals 104 would function in the same way to adopt an inwardly directed shape for introduction of the guide catheter 30 covered by the sheath 52. The petals 104 may displace outwardly when the sheath 52 is withdrawn from its proximal end. The tip is thereby removed from the guide catheter 30.

Figure 23:
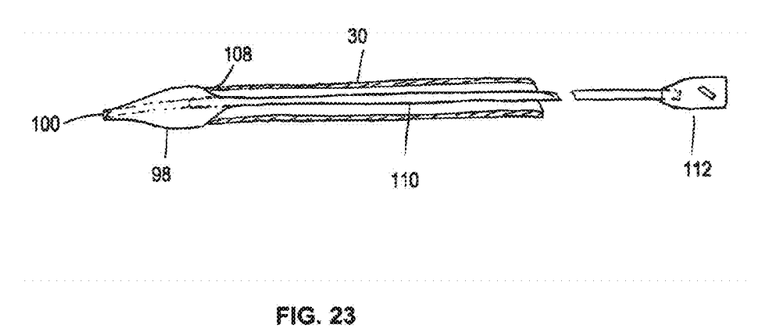
FIG. 23 is a schematic section illustrating an alternative form of separable tip.

In an alternative form (e.g., as illustrated in FIG. 23), the tip 98 may also be separable as a unit from the distal end of the guide catheter 30, and be withdrawable by reverse movement through the delivery lumen of the guide catheter 30. The tip unit 98 may have a proximally-facing guide surface 108 defining a guide shape suitable for allowing smooth withdrawal of the tip 98 through the guide lumen. The guide catheter 30 may optionally expand to permit passage of the tip unit 98 therethrough. The tip unit 56 may be manipulated and/or pulled by means of one or more control wires, or a tube 110 extending within the delivery lumen to the a handle 112 at proximal end of the guide catheter 30.

A method of using and/or operating the guide catheter 30 in a transcatheter aortic valve implantation procedure may generally comprise a step of introducing a distal region 72 of the guide catheter 30 into the vasculature, the guide catheter having a tubular delivery lumen, and advancing the guide catheter such that the distal portion 72 of the guide catheter is placed within the ascending aorta. Optionally, the guide catheter 30 is introduced and advanced with the guide catheter having a collapsed or reduced cross-section size. Optionally, the cross-section size at introduction is smaller than that of a functional catheter referred to below. The guide catheter 30 may, for example, be advanced over a guide wire 26 already inserted into position.

The method may optionally further comprise one, or a combination of any two or more, of following steps. The order of the steps may be varied as desired, and is not limited by the order of description. Some of the steps may be substantially simultaneous or carried out substantially simultaneously:

(a) Removing a sheath 52 constraining the guide catheter 30 to a collapsed state, thereby to permit distension of the guide catheter;

(b) Separating a tip 98 from the distal region of the guide catheter, and withdrawing the tip. The step (b) may be simultaneous with step (a) if, for example, the tip 98 is coupled to the sheath 52. As an alternative example, the tip 98 may be withdrawn via the delivery lumen of the guide catheter 30. In the latter case, if step (a) is included in the method, step (b) may optionally be carried out after step (a).

(c) Introducing a dilation catheter via the delivery lumen of the guide catheter, to a site for, or of, implantation. The dilation catheter may have a dilation device at the distal region thereof. The dilation catheter may be advanced to extend or project beyond the distal end of the guide catheter, such that the dilation device of the dilation catheter is not constrained by the guide catheter. The dilation catheter may be operated to dilate the valve at the implantation site. The step of dilation may optionally be carried out prior to implantation of a replacement valve, in order to dilate a stenosed native valve or a malfunctioning prosthetic valve. Additionally or alternatively, the step of dilation may be carried out following implantation of a replacement valve. Following the or each dilation, the dilation catheter may be withdrawn via the delivery lumen of the guide catheter. For example, following dilation prior to implantation, the dilation catheter may be withdrawn to facilitate step (d) described below.

(d) Introducing a stent-valve delivery catheter via the delivery lumen of the guide catheter to the site of implantation. The delivery catheter may be advanced to extend or project beyond the distal end of the guide catheter, such that implantation of the prosthetic valve is not constrained by the guide catheter. Following implantation, the delivery catheter may be withdrawn via the delivery lumen of the guide catheter.

(e) Deploying and/or controlling an aligner 70 at a distal region of the guide catheter to align the position of at least a portion of the distal region 72 with respect to the ascending aorta. The step of deploying and/or controlling may align the position of at least a portion of the distal region of the guide catheter with respect to a central region of the ascending aorta, for example, with respect to a central axis. In some embodiments, the step of deploying and/or controlling comprises aligning an angle of inclination of the longitudinal axis of the distal region with respect to the ascending aorta.

The step (e) may be carried out prior to steps (c) and/or (d) above. Additionally, the step (e) may be carried out during the steps (c) and/or (d) above, to accommodate and/or compensate for potential distension of the distal region of the guide catheter as a dilation catheter and/or a delivery catheter is passed therethrough.

In a further alternative, step (e) may be simultaneous with step (a) if, for example, the aligner 70 is deployed by removal of the sheath 52.

(f) Placing the aligner in a non-deployed or non-operative configuration after use.

(g) Determining a rotational orientation of the distal region of the guide catheter in the ascending aorta. In some embodiments, the rotational orientation may be determined by manipulating independently one element of the aligner from the proximal end, and observing the rotational orientation of the aligner within the ascending aorta using standard medical imaging apparatus. In other embodiments, the rotational orientation may be determined by imaging predetermined indicia provided at the distal region of the guide catheter.

(h) Introducing a delivery catheter at a proximal end of the guide catheter, the guide catheter being orientated rotationally with respect to the proximal end of the guide catheter in order to be advanced to the distal region of the guide catheter with a desired rotational orientation with respect to the ascending aorta.

(i) deploying a filter to capture any debris introduced into the blood stream by the implantation procedure.

Figure 24:
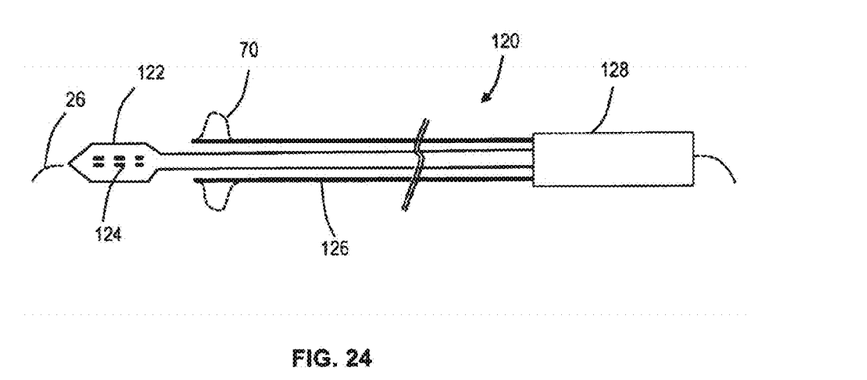
FIG. 24 is a schematic section illustrating the guide catheter and aligner integrated with a functional catheter (delivery catheter).

The above embodiments illustrate use of the invention with or in the form of a guide catheter 30, the guide catheter being distinct from a functional catheter that is inserted through the guide catheter during an implantation procedure. In an alternative form illustrated in FIG. 24, the guide catheter 30 and/or aligner 70 may be incorporated as an integral part of a functional catheter device 120, for example, a dilation catheter or a stent-valve delivery catheter. In this form, the guide catheter 30 and/or the aligner 70 may have any of features described above. For example, the functional catheter 120 may comprise a distal portion 122 for delivering a stent-valve (shown schematically at 124) for implantation. The distal portion 122 may be coupled to a handle portion 128 by a flexible stem 126. The guide catheter 30 may comprise a tube around the stem 126. The guide catheter 30 may permit relative axial displacement of the stem 126 within the guide catheter, for example, to permit manipulation of the distal portion 122 for implanting the stent-valve 124. The guide catheter 30 may carry the aligner 70 for aligning the delivery system near the implantation site prior to advancement of the distal portion 122 to the implantation site. The handle portion 128 may comprise manually operable controls for controlling the aligner 70 and/or the guide catheter 30 and/or the distal portion 122.

Thus the invention also extends generally to apparatus 70 for aligning, within the ascending aorta, a transvascular delivery catheter for delivering a prosthetic valve to an implantation site, the assembly comprising at least one aligner element movable from a non-operative configuration in which the aligner element does not protrude substantially, to an operative configuration in which the aligner protrudes outwardly towards and/or for abutting, the wall of the ascending aorta. The alignment apparatus 70 may be an integral part of the delivery catheter, 110 or it may a supplementary apparatus fitable to the delivery catheter, or within which the delivery catheter may be received. The aligner may be distinct from self-alignment features of an implantable stent carried by the delivery catheter. Such a feature may be significantly advantageous in enabling the position and/or inclination of the delivery catheter to be aligned at or near the implantation site, which in turn may aid implantation of the prosthetic valve.

The invention thus also extends to a method of operating a delivery catheter for transcatheter aortic valve implantation, the method comprising:
  (a) introducing a distal region of the deliver catheter to a site for implantation, via a transvascular access route reaching to and/or through the ascending aorta;
  (b) operating an aligner at or adjacent to the distal region of the delivery catheter for aligning a position and/or inclination of the distal region with respect to the ascending aorta;
  (c) operating the delivery catheter to implant the prosthetic valve at the implantation site.

The step of operating the aligner may include the sub-step of deploying or extending or distending at least one aligner element (and preferably plural aligner elements) to bear against a portion of the wall of ascending aorta. The at least one aligner element may function as a fender to space the delivery catheter from the wall of the ascending aorta at that point, thereby achieving the alignment with respect to the ascending aorta.

It will be appreciated that the foregoing description is merely illustrative of non-limiting preferred embodiments of the invention. Many modifications, improvements and equivalents may be used within the scope of the invention.

The invention claimed is:

1. A flexible guide catheter for use in a transvascular aortic valve replacement procedure, the guide catheter defining a substantially tubular delivery lumen through which one or more other functional catheters may be introduced, wherein the guide catheter comprises a flexible material that permits the lumen of the guide catheter to (i) collapse in cross-section to a compact form for introduction into vasculature constrained within a displaceable sheath, and (ii) distend in cross-section to a distended form to accommodate a maximum size of the one or more other functional catheters introduced therethrough,     wherein the guide catheter is self-biased to be in a stable intermediate form between the compact form and the distended form;

wherein the flexible material comprises a braid or mesh or woven structure of filaments,     wherein the braid or mesh or woven structure comprises open space permitting blood communication therethrough between an exterior and interior of the guide catheter, and     wherein the braid or mesh or woven structure permits distension to the distended form by rearrangement of the filaments without substantial elastic stretching of the filaments.

2. The guide catheter of claim 1, wherein the guide catheter has a generally round cross-sectional shape in both the compact form and the distended form.

3. The guide catheter of claim 1, further comprising a sleeve sealed to the flexible material of the guide catheter at or near a proximal end of the flexible material, and extending at least 20 mm distally along a length of the flexible material, the sleeve being elastically stretchable to accommodate expansion of the guide catheter when the at least one other functional catheter is introduced therethrough.

4. The guide catheter of claim 1, further comprising, at least initially for introduction into the vasculature, a tapered or rounded tip at a distal region of the guide catheter.

5. The guide catheter of claim 1, wherein the flexible material of the guide catheter is selected from: silicone, polyether block amide, metal, stainless steel, and nitinol.

* * * * *